United States Patent
Schmalstieg et al.

(10) Patent No.: US 6,703,453 B1
(45) Date of Patent: Mar. 9, 2004

(54) CONDENSATION CROSS-LINKING POLYURETHANE MATERIALS CONTAINING SPECIAL AMINOSILANES, A METHOD FOR THE PRODUCTION THEREOF AND THEIR USE

(75) Inventors: Lutz Schmalstieg, Köln (DE); Ralf Lemmerz, Leverkusen (DE); Ulrich Walter, deceased, late of Langenfeld (DE), by Marie-Hélène Marie-Ange Christiane Walter, legal representative; Oswald Wilmes, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/019,578

(22) PCT Filed: Jun. 13, 2000

(86) PCT No.: PCT/EP00/05392

§ 371 (c)(1),
(2), (4) Date: Dec. 21, 2001

(87) PCT Pub. No.: WO01/00700

PCT Pub. Date: Jan. 4, 2001

(30) Foreign Application Priority Data

Jun. 25, 1999 (DE) .......................................... 199 29 029
Jun. 25, 1999 (DE) .......................................... 199 29 011

(51) Int. Cl.⁷ ........................ C08G 77/18; C08G 18/61; C08L 83/06; C08L 75/04

(52) U.S. Cl. ...................... 525/453; 524/425; 524/788; 525/454; 525/477; 528/12; 528/14; 528/33; 528/34; 528/38; 528/41; 528/43

(58) Field of Search ................. 524/425, 788; 525/453, 454, 477; 528/12, 14, 33, 34, 38, 41, 43

(56) References Cited

U.S. PATENT DOCUMENTS 6,197,912 B1 * 3/2001 Huang et al. ................. 528/28

FOREIGN PATENT DOCUMENTS

| EP | 596 360 | 5/1994 |
| EP | 807 649 | 11/1997 |
| EP | 831 108 | 3/1998 |
| EP | 864 575 | 11/1998 |
| EP | 0 676 403 | 9/1999 |
| EP | 994 138 | 4/2000 |

* cited by examiner

*Primary Examiner*—Rabon Sergent
(74) *Attorney, Agent, or Firm*—Joseph C. Gil; Thomas W. Roy; Gary F. Matz

(57) ABSTRACT

This invention relates to polyurethane compositions which cross-link via a silane polycondensation and contain at least one alkoxysilane-functional polyurethane, at least one basic filler, at least one reaction product of an aminosilane with a maleic or fumaric ester, at least one organometallic compound and optionally additional auxiliary substances, to a process for their preparation, and to their use.

11 Claims, No Drawings

CONDENSATION CROSS-LINKING POLYURETHANE MATERIALS CONTAINING SPECIAL AMINOSILANES, A METHOD FOR THE PRODUCTION THEREOF AND THEIR USE

BACKGROUND OF THE INVENTION

This invention relates to polyurethane compositions which cross-link via a silane polycondensation and contain at least one alkoxysilane-functional polyurethane, at least one basic filler, at least one reaction product of an aminosilane with a maleic or fumaric ester, at least one organometallic compound and optionally additional auxiliary substances, to a process for their preparation, and to their use.

Alkoxysilane-functional polyurethanes which cross-link via a silane polycondensation are part of long-known prior art. A survey of the topic is to be found in "Adhesives Age" 4/1995, page 30 ff. (authors: Ta-Min Feng. B. A. Waldmann). Such alkoxysilane-terminated, moisture-curing one-component polyurethanes are increasingly being used as flexible elastic coating, sealing and adhesive compositions in the construction industry and in the automobile industry. For these applications, high demands are placed on the extensibility, the adhesive power and on the speed of cure.

Such products are described by way of example in EP-A 596360, EP-A 831108, EP-A 807649 or in EP-A 676403. Organometallic catalysts as well as adhesion promoters of the aminosilane type are commonly used concomitantly in the formulation of systems of this kind. But the addition of aminosilane compounds can often lead to problems with stability in storage, particularly when higher proportions of aminosilanes are used in order to achieve a good adhesion to difficult substrates.

Accordingly, the object of the present invention was to provide polyurethane compositions which cross-link via a silane polycondensation, contain aminosilanes and have an improved stability in storage.

This object was achieved by the provision of the polyurethane compositions which cross-link by condensation described in more detail below.

SUMMARY OF THE INVENTION

The invention provides polyurethane compositions which cross-link via a silane polycondensation, containing A) at least one alkoxysilane-functional polyurethane having end groups corresponding to the general formula (I)

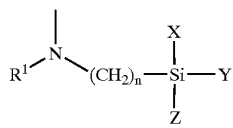

(I), wherein
$R^1$ represents an organic group having 1 to 12 carbon atoms,
n is an integer from 2 to 4 and
X, Y, Z denote identical or different organic groups, with the proviso that at least one of the groups is an alkoxy group having 1 to 4 carbon atoms, preferably a methoxy or ethoxy group, B) at least one basic filler,
C) at least one reaction product of at least one aminosilane corresponding to the general formula (II)

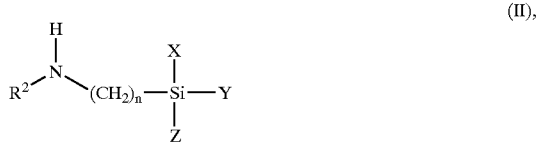

(II), wherein
$R^2$ represents a hydrogen atom, or an aminoethyl group and
n, X, Y, Z have the meanings given for formula (I),
with at least one maleic or fumaric (ester) corresponding to the general formula (III)

$$R_3OOC-CH=CH-COOR_3 \qquad (III),$$

wherein
$R_3$ represents an alkyl group having 1 to 12 carbon atoms,
E) at least one organometallic compound and
F) optionally additional auxiliary substances.

DETAILED DESCRIPTION OF THE INVENTION

The invention is based on the surprising observation that the adducts of aminosilanes with maleic or fumaric esters which, according to the invention, are used instead of the aminosilanes conventionally employed as adhesion promoters, bring about improved mechanical properties and an improved stability in storage.

The reaction products of maleic or of fumaric esters and aminosilanes which according to the invention are to be used as component C) are known in principle and are described by way of example in EP-A 596360 or EP-A 831108. According to the disclosures in these publications, the reaction products of maleic or of fumaric esters with aminosilanes are used for the reaction with isocyanate prepolymers. The use of these products as an additive for improving the mechanical properties and for improving the adhesion of polyurethanes which cross-link via silane polycondensation is hitherto unknown.

The polyurethanes having alkoxysilane end groups which according to the invention are to be used as component A) are known in principle and are prepared by reacting long-chain, preferably linear, NCO prepolymers with aminofunctional silanes corresponding to the general structural formula (II)

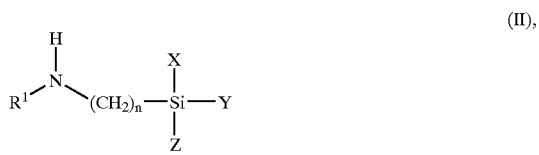

(II), wherein $R^1$ represents an organic group having 1 to 12 carbon atoms, preferably a phenyl group or particularly preferably a group corresponding to the general structural formula (IIb),

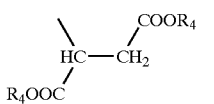
(IIb), wherein $R_4$ represents an alkyl group having 1 to 4 carbon atoms. In the above structural formula, n is an integer from 2 to 4, preferably 3.

X, Y, Z in the above structural formula denote identical or different organic groups, with the proviso that at least one of the groups is an alkoxy group having 1 to 4 carbon atoms. Preferably at least one of the groups is a methoxy or ethoxy group. Particularly preferably X, Y and Z each represent a methoxy group.

Examples of suitable aminofunctional silanes producing end groups corresponding to structural formula (I) are N-methyl-3-aminopropyltrimethoxysilane. N-methyl-3-aminopropyltriethoxysilane, N-butyl-3-aminopropyltrimethoxysilane. The use of N-phenyl-3-aminopropyltrimethoxysilane is preferred. It is particularly preferable to use the aspartic esters described in EP-A 596360. which are formed through the reaction of aminosilanes corresponding to the general structural formula (II) with maleic or fumaric esters corresponding to formula (III).

NCO prepolymers which can be used for the preparation of the polyurethanes A) having alkoxysilane end groups are prepared in known per se manner by reacting polyether polyols, preferably polyether diols, with diisocyanates and have an NCO content of between 0.4 and 4%.

Compounds which can be used as basic fillers B) are precipitated or ground chalks, metal oxides, metal sulfates, metal silicates, metal hydroxides, metal carbonates and metal hydrogen carbonates. Other fillers are, for example, reinforcing and non-reinforcing fillers such as, for example, pyrogenic or precipitated silicas, carbon black or quartz powder. Both the basic fillers and the other reinforcing or non-reinforcing fillers may optionally be surface-modified. Precipitated or ground chalks and pyrogenic silicas are particularly preferably used as basic fillers B). The component B) may, of course, also be mixtures of fillers.

Compounds used as component C) are reaction products of aminosilane compounds corresponding to the general structural formula (II)

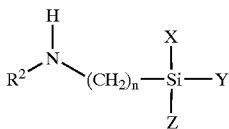
(II), wherein
$R^2$, X, Y, Z and n have the meanings given above,
with maleic or fumaric (esters) corresponding to the general formula (III)

$R_3OOC—CH=CH—COOR_3$ (III), wherein
$R_3$ represents an alkyl group having 1 to 12 carbon atoms.

Examples of usable aminosilane compounds corresponding to formula (II) are 3-aminopropyltrimethoxysilane, 3-aminopropyltriethoxysilane, N-aminoethyl-3-aminopropyltrimethoxysilane, N-aminomethyl-3-aminopropyltriethoxysilane, 3-amino-propylmethyldiethoxysilane and N-aminoethyl-3-aminopropylmethyldimethoxysilane.

In formula (III), $R_3$ represents a linear or branched aliphatic hydrocarbon group having at most 12 carbon atoms. Examples of suitable maleic and fumaric esters are diethyl maleate, dimethyl maleate, dibutyl maleate, dioctyl maleate, diethyl fumarate, dimethyl fumarate, dioctyl fumarate.

In the case where the products in which $R_2$ in formula (II) denotes a hydrogen atom are used as aminosilanes, in the course of the reaction with the maleic or fumaric esters in accordance with the disclosure in EP-A 596360, aspartic esters corresponding to the general structural formula (IV) are formed

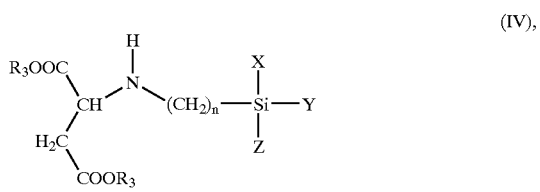
(IV), wherein
$R^3$, X, Y, Z and n have the meanings given for formulae (II) and (III).

In the particularly preferred case, where products in which $R_2$ denotes an aminoethyl group are used as aminosilanes corresponding to formula (II), piperazinone derivatives corresponding to the general formula (V)

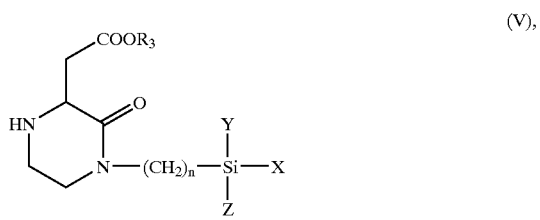
(V), wherein
$R_3$, X, Y, Z and n have the meanings given for formula (IV),
are formed through a cyclocondensation reaction.

All organometallic catalysts, which—as is generally known—promote silane polycondensation, can be used as component E). These are in particular compounds of tin and of titanium. Preferred tin compounds are, for example, dibutyltin dilaurate, dibutyltin diacetate and dioctyltin maleate, tin(II) octoate or dibutyltin bis(acetoacetonate). Preferred titanium compounds are, for example, alkyl titanates, such as tetraisopropyl titanate, tetrabutyl titanate and chelated titanium compounds, such as ethyl diisobutylbis(acetoacetate) titanate. Dibutyltin bis (acetoacetonate) is particularly preferably used as component E).

Additives and auxiliary substances F) according to the invention which may be mentioned are drying agents, plasticisers, adhesives other than those mentioned under D), thixotropic agents, light stabilisers, pigments and protective agents, for example, fungicides.

Drying agents to be mentioned in particular are alkoxysilyl compounds, such as vinyltrimethoxysilane, methyltrimethoxysilane, i-butyltrimethoxysilane, hexadecyltrimethoxysilane. Examples of plasticisers which may be given are phthalic esters, adipic esters, alklylsulfonic esters of phenol or phosphate esters. Examples of thixotropic agents which may be vixen arc polyamides, hydrogenated products of castor oil or even polyvinyl chloride. Aminosilanes of the knows kind, epoxysilanes and/or mercaptosilanes can be used as adhesion promoters in addition to the compounds mentioned under C).

The polyurethane compositions according to the invention consist preferably of 30 to 80 wt. % of component A), 10 to 50 wt. % of component B), 0.5 to 3 wt. % of component C), 0.02 to 1 wt. % of component D) and 0 to 40 wt. % of component F).

The present invention also provides a process for the preparation of the polyurethane compositions according to the invention which cross-link by condensation. In the process according to the invention, component C) is prepared in a separate reaction vessel by reacting the aminosilanes with the maleic or fumaric esters, similarly to the disclosure in EP-A 596360, in the temperature range of 0° C. to 100° C. Components A), B), D) and optionally E) are mixed together, with exclusion of moisture, and component C) is then added thereto.

In a preferred embodiment of the process according to the invention, the component C) used according to the invention is produced in situ. In this procedure, components A), B), D) and optionally E), together with the maleic or fumaric esters used for the preparation of C), are mixed together, with exclusion of moisture, and the aminosilanes used according to the invention to prepare component C) are then added thereto.

The present invention also provides the use of the reaction products of aminosilanes and maleic and fumaric esters, which can be used according to the invention as component C), as an additive in polyurethane compositions which cross-link by condensation.

The present invention further provides the use of the polyurethane compositions according to the invention which cross-link by condensation as sealant, adhesive or coating material.

The polyurethane compositions according to the invention which cross-link by condensation on the one hand exhibit a rapid cure with skin formation times of between 15 and 120 minutes, but on the other hand have excellent stability in storage in the temperature range of up to 60° C.

The cross-linked polymers exhibit improved mechanical properties, in particular an improved elongation at tear as compared with similar systems containing conventional aminosilanes. Moreover, the polyurethane compositions according to the invention are distinguished by having excellent adhesion, in particular wet adhesion, to all conceivable substrates such as, for example, metal, ceramic, plastics, stone or concrete.

EXAMPLES

Preparation of a Polyurethane A1) Having Alkoxysilyl End Groups 2000 g of a polyether diol having an OH value of 28, prepared by propoxylation of propylene glycol and subsequent ethoxylation of the propoxylation product (PO/EO ratio=80:20), was prepolymerised with 155.4 g isophorone diisocyanate at 70° C., with addition of 0.02 g dibutyltin dilaurate, until the theoretical NCO content of 0.78% was attained. The reaction mixture was cooled to 60° C., then 140.4 g N-(3-trimethoxysilylpropyl)aspartic acid, diethyl ester (prepared as in EP-A 596360, Example 5) was added speedily and the mixture stirred until isocyanate bands were no longer to be seen in the IR spectrum. The resulting polyurethane prepolymer with alkoxysilyl end groups had a viscosity of 76000 mPas (23° C.).

Preparation of a Polyurethane A2) Having Alkoxysilyl End Groups 2000 g of a polyether diol having an OH value of 28, prepared by propoxylation of propylene glycol and subsequent ethoxylation of the propoxylation product (PO/EO ratio=80:20), was prepolymerised with 155.4 g isophorone diisocyanate at 70° C., with addition of 0.02 g dibutyltin dilaurate, until the theoretical NCO content of 0.78% was attained. The reaction mixture was cooled to 60° C., then 102 g N-phenyl-3-aminopropyltrimethoxysilane was added speedily and the mixture stirred until isocyanate bands were no longer to be seen in the IR spectrum. The resulting polyurethane prepolymer with alkoxysilyl end groups had a viscosity of 86000 mPas (23° C.).

Example 1

Preparation of a Polyurethane Composition According to the Invention

In a commercial planetary mixer, the following components were processed to produce a ready-to-use sealant:

36.4 parts by wt. polyurethane A1)

12.9 parts by wt. diisoundecyl phthalate (plasticiser)

0.02 parts by wt. dibutyltin bis(acetoacetonate) (10% dissolved in solvent naphtha 100)

1.50 parts by wt. vinyltrimethoxysilane.

46.2 parts by wt. precipitated chalk (type: Socal® U1S2)

2.00 parts by wt. diethyl maleate 1.40 parts by wt. Disparlon® NVG8403 S (thixotropic agent from Kusumoto Chem. Ltd.)

The mixture was dispersed for 10 minutes at a pressure of 100 mbar, during which the internal temperature rose to 60° C. Then 1.5 parts by wt. N-aminoethyl-3-aminopropyltrimethoxysilane was added and worked in by stirring for 10 minutes at a pressure of 100 mbar. The sealant thus prepared had excellent stability, bonded to virtually all substrates and cured with a skin formation time of 30 minutes.

The product was packed into a commercial cartridge and stored at 50° C. After a storage period of 90 days, the product could still be processed without difficulty and exhibited no changes in its properties.

The following mechanical properties were determined:

| Tensile strength | 2.6 N/mm$^2$ | (DIN 53504) |
| Elongation at break | 268% | (DIN 53504) |
| Tear propargation resistance | 5.4 N/mm | (DIN 53515) |
| Shore A hardness | 42 | |

Example 2

Preparation of a Polyurethane Composition According to the Invention

In a commercial planetary mixer, the following components were processed to produce a ready-to-use sealant:

36.0 parts by wt. polyurethane from Example 2

12.6 parts by wt. diisoundecyl phthalate (plasticiser)

0.02 parts by wt. dibutyltin bis(acetoacetonate) (10% dissolved in solvent naphtha 100)

2.20 parts by wt. vinyltrimethoxysilane 45.68 parts by wt. precipitated chalk (type: Socal® U1S2 from Solvay GmbH)

2.00 parts by wt. dimethyl maleate 1.40 parts by wt. Cabosil® TS 720 (pyrogenic silica from Cabot GmbH)

The mixture was dispersed for 10 minutes at a pressure of 100 mbar, during which the internal temperature rose to 60° C. Then 2.1 parts by wt. N-aminoethyl-3-aminopropyltrimethoxysilane was added and worked in by stirring for 10 minutes at a pressure of 100 mbar.

The sealant thus prepared had excellent stability, bonded to virtually all substrates and cured with a skin formation time of 40 minutes.

The product was packed into a commercial cartridge and stored at 50° C. After a storage period of 90 days, the product could still be processed without difficulty and exhibited no changes in its properties.

The following mechanical properties were determined:

| Tensile strength | 28 N/mm² | (DIN 53504) |
| Elongation at break | 290% | (DIN 53504) |
| Tear propargation resistance | 7.5 N/mm | (DIN 53515) |
| Shore A hardness | 46 | |

Example 3

Comparison Example not According to the Invention

Example 1 was repeated, with the difference that no diethyl maleate was added. The product was packed into a commercial cartridge and stored at 50° C. After a storage period of 60 days, the product could no longer be squeezed out of the cartridge and had gelled.

The following mechanical properties were determined:

| Tensile strength | 2.5 N/mm² | (DIN 53504) |
| Elongation at break | 235% | (DIN 53504) |
| Tear propargation resistance | 5.6 N/mm | (DIN 53515) |
| Shore A hardness | 42 | |

Example 4

Comparison Example not According to the Invention

Example 2 was repeated with the difference that no dimethyl maleate was added. The product was packed into a commercial cartridge and stored at 50° C. After a storage period of 35 days, the product could no longer be squeezed out of the cartridge and had gelled.

The following mechanical properties were determined:

| Tensile strength | 2.8 N/mm² | (DIN 53504) |
| Elongation at break | 250% | (DIN 53504) |
| Tear propargation resistance | 7.4 N/mm | (DIN 53515) |
| Shore A hardness | 46 | |

Example 5

Preparation of a Polyurethane Composition According to the Invention

In a commercial planetary mixer, the following components were processed to produce a ready-to-use sealant:

36.4 parts by wt. polyurethane A1)

12.9 parts by wt. diisoundecyl phthalate (plasticiser)

0.04 parts by wt. dibutyltin bis(acetoacetonate) (10% dissolved in solvent naphtha 100)

1.50 parts by wt. vinyltrimethoxysilane 46.2 parts by wt. precipitated chalk (tripe: Socal® U1S2)

1.40 parts by wt. Disparlon® NVG8403 S (thixotropic agent from Kusumoto Chem. Ltd.)

The mixture was dispersed for 10 minutes at a pressure of 100 mbar, during which the internal temperature rose to 60° C. Then 2.5 parts by wt. N-(3-trimethoxysilylpropyl)aspartic acid, diethyl ester (prepared as in EP-A 596360, Example 5)

was added and worked in by stirring for 10 minutes at a pressure of 100 mbar.

The sealant thus prepared had excellent stability, bonded to virtually all substrates and cured with a skin formation time of 50 minutes.

The product was packed into a commercial cartridge and stored at 50° C. After a storage period of 90 days, the product could still be processed without difficulty and exhibited no changes in its properties.

The following mechanical properties were determined:

| Tensile strength | 2.5 N/mm² | (DIN 53504) |
| Elongation at break | 310% | (DIN 53504) |
| Tear propargation resistance | 6.1 N/mm | (DIN 53515) |
| Shore A hardness | 39 | |

What is claimed is:

1. A polyurethane composition which cross-links via silane polycondensation and comprises A) at least one alkoxysilane-functional polyurethane having end groups corresponding to formula (I)

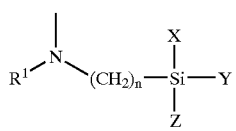

(I), wherein $R^1$ represents an organic group having 1 to 12 carbon atoms, n is an integer from 2 to 4 and X, Y, Z represent identical or different organic groups, provided that at least one of the groups is an alkoxy group having 1 to 4 carbon atoms, B) at least one filler,
C) at least one reaction product of
   i) at least one aminosilane corresponding to formula (II)

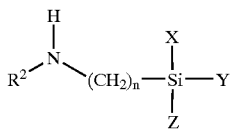
(II), wherein
   $R^2$ represents an aminoethyl group
   n is an integer from 2 to 4
   X, Y, Z have the meanings set forth for formula (I), with
   ii) at least one maleic or fumaric ester corresponding to formula (III)

$R^3OOC-CH=CH-COOR^3$ (III), wherein
   $R^3$ represents an alkyl group having 1 to 12 carbon atoms, and
D) at least one organometallic compound.

2. The polyurethane composition of claim 1 wherein $R^1$ represents a group corresponding to formula (IIb)

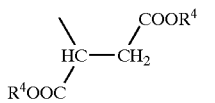
(IIb), wherein $R^4$ denotes an alkyl group having 1 to 4 carbon atoms.

3. The polyurethane composition of claim 1 wherein component C) comprises an aminosilane compound corresponding to formula (V)

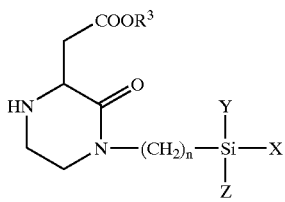
(V), wherein
   $R^3$ represents a linear or branched aliphatic hydrocarbon group having at most 12 carbon atoms,
   n is 3 and
   X, Y and Z represent methoxy or ethoxy groups.

4. The polyurethane composition of claim 1 wherein X, Y and Z each represent a methoxy or ethoxy group.

5. The polyurethane composition of claim 2 wherein X, Y and Z each represent a methoxy or ethoxy group.

6. The polyurethane composition of claim 3 wherein X, Y and Z each represent a methoxy or ethoxy group.

7. The polyurethane composition of claim 1 wherein X, Y and Z each represent a methoxy group in component A).

8. The polyurethane composition of claim 2 wherein X, Y and Z each represent a methoxy group in component A).

9. The polyurethane composition of claim 3 wherein X, Y and Z each represent a methoxy group in component A).

10. A process for the preparation of the polyurethane composition of claim 1 which comprises mixing components A), B), and D) with exclusion of moisture and subsequently adding component C, the reaction product of i) and ii).

11. A polyurethane composition which cross-links via silane polycondensation and comprises
   A) at least one alkoxysilane-functional polyurethane having end groups corresponding to formula (I)

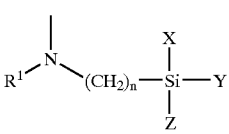
(I), wherein
   $R^1$ represents a group corresponding to formula (IIb)

(IIb), wherein $R^4$ represents an ethyl group,
   n is 3 and
B) at least one filler,
C) at least one reaction product of
   i) at least one aminosilane corresponding to formula (II)

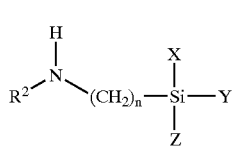
(II), wherein
   $R^2$ represents an aminoethyl group and
   n, X, Y, Z have the meanings set forth for formula (I), with
   ii) at least one maleic or fumaric ester corresponding to formula (III)

$R^3OOC-CH=CH-COOR^3$ (III), wherein
   $R^3$ represents an alkyl group having 1 to 12 carbon atoms, and
D) at least one organometallic compound.

* * * * *

UNITED STATES PATENT AND TRADEMARK OFFICE
CERTIFICATE OF CORRECTION

PATENT NO. : 6,703,453 B1
DATED : March 9, 2004
INVENTOR(S) : Lutz Schmalstieg et al.

It is certified that error appears in the above-identified patent and that said Letters Patent is hereby corrected as shown below:

Column 10,
Line 35, insert -- X, Y, Z represent methoxy or ethoxy groups, --.

Signed and Sealed this

Twenty-second Day of February, 2005

JON W. DUDAS
*Director of the United States Patent and Trademark Office*